United States Patent [19]

Drain et al.

[11] Patent Number: 4,492,467

[45] Date of Patent: Jan. 8, 1985

[54] MEASUREMENT OF THE SIZE OF PARTICLES

[75] Inventors: Leslie E. Drain, Goring on Thames; Clive R. Negus, Stanford in the Vale, both of England

[73] Assignee: United Kingdom Atomic Energy Authority, London, England

[21] Appl. No.: 381,855

[22] Filed: May 25, 1982

[30] Foreign Application Priority Data

Jun. 4, 1981 [GB] United Kingdom ................ 8117190

[51] Int. Cl.³ ............................................ G01N 15/02
[52] U.S. Cl. .................... 356/336; 356/340; 356/342; 356/343; 356/364
[58] Field of Search ............... 356/336, 338, 339, 340, 356/341, 342, 343, 364, 365; 250/225, 227

[56] References Cited

U.S. PATENT DOCUMENTS

| | | | |
|---|---|---|---|
| 3,653,767 | 4/1972 | Liskowitz | 356/342 X |
| 3,835,315 | 9/1974 | Gravitt, Jr. | 250/227 X |
| 4,173,415 | 11/1979 | Wyatt | 356/336 |
| 4,286,876 | 9/1981 | Hogg et al. | 356/343 |
| 4,385,830 | 5/1983 | Webb et al. | 356/338 X |

Primary Examiner—Davis L. Willis
Assistant Examiner—Matthew W. Koren
Attorney, Agent, or Firm—William R. Hinds

[57] ABSTRACT

A method of determining the size of spherical particles, comprising the operations of illuminating with a beam of circularly polarized light particles the size of which is to be determined, detecting light backscattered by the particles, measuring the angular intensity distribution of the backscattered light and deriving therefrom an indication of the size of the particles.

Various forms of apparatus for carrying out the method also are described.

4 Claims, 8 Drawing Figures

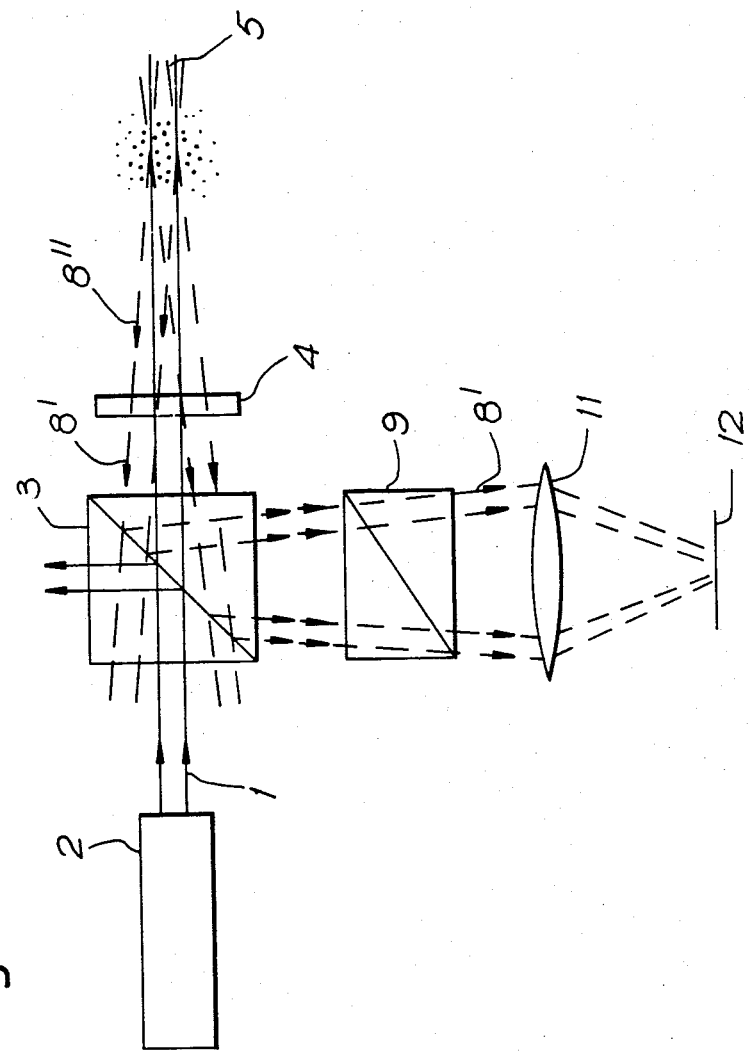

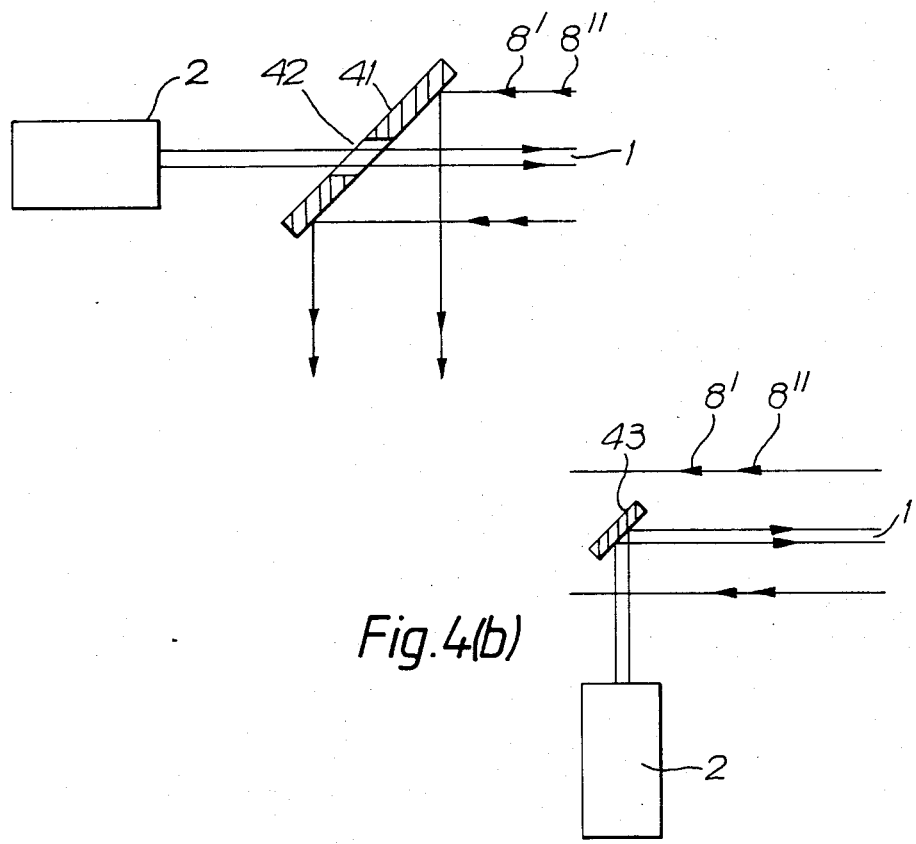
Fig. 4(a)
Fig. 4(b)
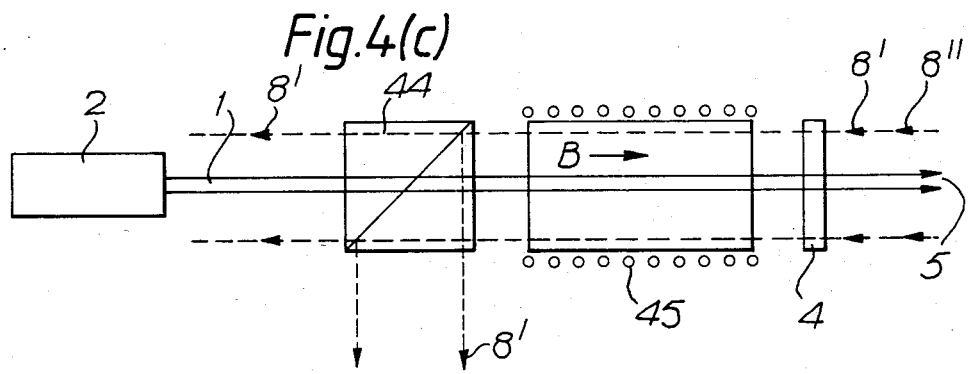
Fig. 4(c)

MEASUREMENT OF THE SIZE OF PARTICLES

The present invention relates to the measurement of the size of spherical particles.

In the context of the present specification, the term 'particles' is intended to apply both to solid bodies and to drops of liquids.

A number of optical methods for measuring the size of particles are available. For example, the diameters of projected images of the particles can be measured directly. More sophisticated techniques utilise the variations in the intensity of light which is scattered by the particles as they traverse a system of interference fringes, or the intensity distribution of unpolarised light scattered by the particles in a forward direction.

The present invention bears some similarity to the last mentioned technique, but it operates in a backscatter mode which simplifies the optical arrangements, because only one-sided optical access is required.

According to the present invention there is provided a method of determining the size of spherical particles, comprising the operations of illuminating with a beam of circularly polarised light particles the size of which is to be determined, detecting light backscattered by the particles, measuring the angular intensity distribution of the backscattered light and deriving therefrom an indication of the sizes of the particles.

Also according to the invention there is provided an apparatus for determining the size of spherical particles, comprising, means for illuminating with a beam of circularly polarised light particles the size of which is to be determined, means for detecting light backscattered from the illuminating beam by the particles and means for measuring the angular distribution of the backscattered light.

Preferably the illuminating beam of circularly polarised light is derived from a laser source.

The invention will now be explained and described, by way of example, with reference to the accompanying drawings, in which:

FIG. 3 shows another apparatus embodying the invention,

Figure 2:
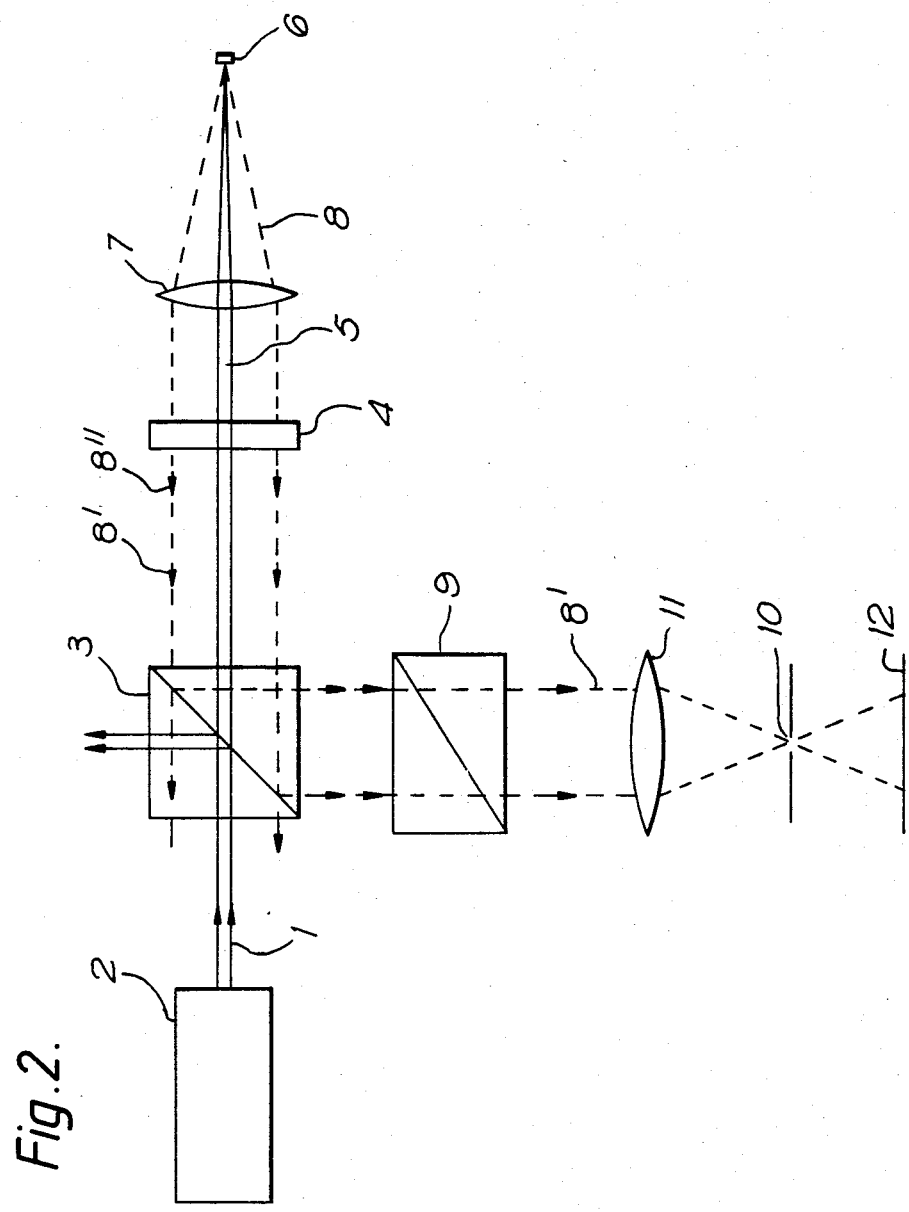
FIG. 2 shows an apparatus embodying the invention.
Figure 5A:
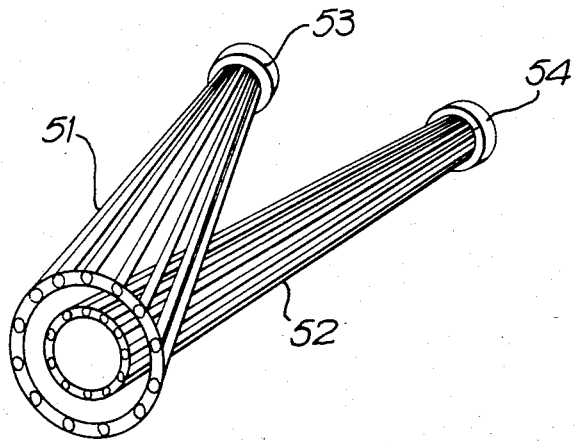
Figure 5B:
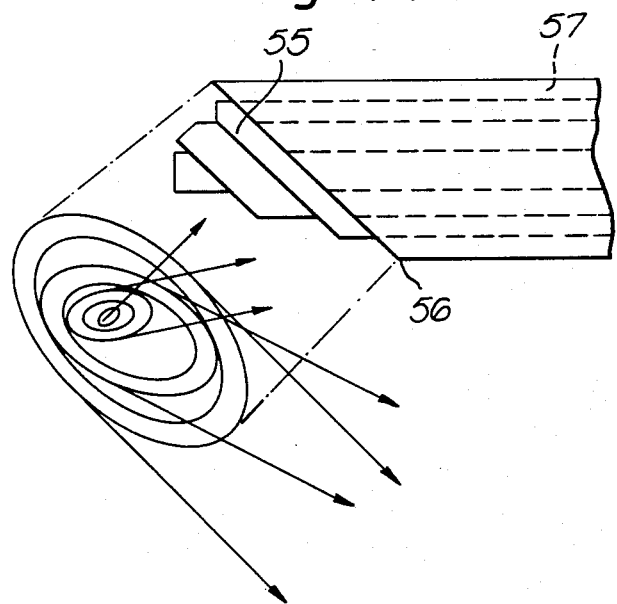

FIGS. 4(a), 4(b), and 4(c) show three further ways of illuminating the particles the size of which is to be determined, which can be incorporated with either the apparatus of FIG. 2 or that of FIG. 3, and FIGS. 5(a) and 5(b) show diagrammatically two forms of detector which are suitable for use in the apparatus of FIG. 2 or of FIG. 3.

If $S_1(\theta)$ and $S_2(\theta)$ are the scattering functions for the electric field components of a plane electromagnetic wave which is scattered by a spherical particle, normal and perpendicular to the scattering plane, then it can be shown that for a circularly polarised incident beam, the scattered intensity in the backward direction is given by:

$$\overset{\frown}{I} = \sigma\{S_1+S_2\}^2/4$$

and $$\overset{\frown}{\overset{\frown}{I}} = \sigma\{S_1-S_2\}^2/4$$

where $\overset{\frown}{I}$ is the scattered intensity component rotating in the same sense as the beam which was incident upon the scattering particle when viewed from the same direction in space. $\overset{\frown}{\overset{\frown}{I}}$ is the intensity of the counter-rotating component and $$\sigma = \lambda^2 I_o / 4\pi^2 \gamma^2$$

where $\lambda$ is the wavelength of the incident light, $I_o$ its intensity and $\gamma$ the distance from the scattering particle. The functions $S_1(\theta)$ and $S_2(\theta)$ were first determined by Mie in a paper published in Ann. d. Physik (4) 25 p 377.

Figure 1:
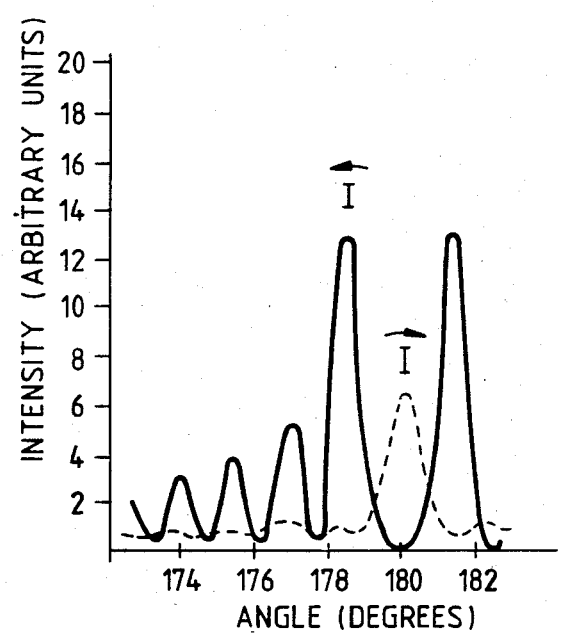
FIG. 1 shows the angular distribution of light backscattered by a particle.

FIG. 1 shows the intensities $\overset{\frown}{I}$ and $\overset{\frown}{\overset{\frown}{I}}$ plotted as functions of the scattering angle $\theta$ for particles having a diameter of approximately 39λ and a refractive index of 1.43.

It can be seen that the function $\overset{\frown}{I}(\theta)$ has peaks which are regularly spaced, unlike those which occur in the function $\overset{\frown}{\overset{\frown}{I}}(\theta)$.

It can be shown on the basis of geometrical optics and diffraction theory that the positions of the backscattered peaks are given by the relatively simple expression $$\overset{\frown}{I}(\theta) \alpha [J_2[(2\pi a \sin\theta^+)/\lambda]]^2$$

where $J_2$ is the second order Bessel function, a is the particle radius, λ is the wavelength of the light and $\theta^{30}$ is the backscatter angle.

FIGS. 2 and 3 illustrate two forms of apparatus for putting the invention into practice. That arrangement which is illustrated in FIG. 2, gives 3-dimensional spatial resolution which is suitable particularly for sizing single particles in low density situations. That arrangement which is illustrated in FIG. 3 gives only line of sight resolution but is more suitable for use when many particles are under observation.

Referring to FIG. 2, a narrow plane polarised beam of light 1 from a laser source 2 is passed through a beam splitter 3 and then a quarter wave plate 4 which converts it into a circularly polarised beam of light 5 which is brought to a focus on a scattering particle 6 by means of a lens 7. Scattered light 8 containing components rotating in the same and opposite senses as the light in the beam 5 are converted into two superimposed beams 8' and 8" with their electric field vectors $E_x$ and $E_y$ in and perpendicular to the plane of the paper, respectively. The beam splitter 3 directs the beams of light 8' and 8" onto a polarisation analyser 9, for example, a Nicol prism, which selects the counter-rotating beam 8' only. This is brought to a focus at an aperture 10 by means of a lens 11, and then falls on an annular shaped detector 12.

The apparatus shown in FIG. 3 is similar to that shown in FIG. 2, and corresponding components have the same reference numbers. The differences are than the lens 7 and the aperture 10 are omitted. Also, the detection system 12 is in the Fourier transform plane of the lens 11, and it is arranged to be sensitive only to the angular deviation of the scattered light. Thus the position of any given scattering particle along the axis of the beam of lights is unimportant within the limits of the backscattered light collection aperture.

When a single particle is in the beam of light 5, the scattered light level is low, also the form of beam splitter shown in FIGS. 2 and 3 utilises at most a quarter of the available light passing through it. For use in these circumstances, one or other of the arrangements shown in FIGS. 4(a) to (c) can be adopted. The arrangement shown in FIG. 4(a) utilises a mirror 41 with a central aperture 42. The arrangement shown in FIG. 4(b) utilises a small mirror 43 which acts on the beam light 1 from the laser source 2. The backscattered light is not deflected at all. Both the arrangement shown in FIG. 4(a) and that shown in FIG. 4(b) have the disadvantage of obscuring the centre of the scattered ring system.

The arrangement shown in FIG. 4(c) is more complicated. It uses a polarising beam splitter 44 with a Faraday rotator 45, and does not use the polarisation analyser 9. The physical size of the extra components and the power required by the Faraday rotator 45 are disadvantages of this system.

FIG. 5(a) shows two forms of annular detector which can be used. The arrangement shown in FIG. 5(a) uses concentric annular bundles of optical fibres, two of which are shown. Each annular group of fibres 51 and 52 is brought to a circular output at a respective light sensitive diode 53 and 54. Alternatively, the photo diodes 53 and 54 can be replaced by photomultipliers.

FIG. 5(b) shows another form of annular detector. The annular detector shown in FIG. 5(b) consists of a plurality of elliptical mirrors 55 which are regularly displaced relatively to one another in azimuth.

A plurality of light sensitive diodes or photomultipliers (not shown) are positioned at known angular locations so as to receive light reflected from the mirrors 55. The mirrors 55 are produced by working an end 56 of a bundle of co-axial tubes 57 at an angle of 45° to the axis of the bundle of co-axial tubes 57, rotating the tubes 57 relative to one another and fixing them in the desired positions.

Other forms of detector which are not illustrated are an annular array of self-scanning storage light sensitive diodes, or a spirally scanned television tube.

The final determination of particle size can be achieved either by carrying out a Fourier transform process on the outputs from the detectors electronically, or by means of a suitable computer program.

We claim:

1. A method of determining the size of spherical particles, comprising the operations of illuminating a volume of space including spherical particles, the size of which is to be measured, with circularly polarized light having a given direction of rotation of its electric vector, detecting circularly polarized light backscattered from the particles and having the direction of rotation of its electric vector opposite to that of the incident light, measuring the angular distribution of the intensity of the said backscattered light, and deriving therefrom the size of the particles.

2. Apparatus for determining the size of spherical particles, comprising means for illuminating a volume of space including spherical particles, the size of which is to be measured, with circularly polarized light having a given direction of rotation of its electric vector, means for selecting from light backscattered by the particles that which has its electric vector rotating in a direction opposite to that of the incident light, and means for measuring the angular variations in the intensity of the said selected backscattered light.

3. Apparatus according to claim 2 wherein the means for measuring the angular variations in the intensity of the selected backscattered light comprises a lens and an angularly discriminating detector system situated in the Fourier transform plane of the lens.

4. Apparatus according to claim 2 wherein the means for measuring the angular variations in the intensity of the selected backscattered light comprises means for bringing the light to a focus at an aperture, and an angularly discriminating detector system arranged to receive light which has passed through the aperture.

* * * * *